United States Patent [19]

Fukushima et al.

[11] Patent Number: 5,336,798
[45] Date of Patent: Aug. 9, 1994

[54] PREPARATION OF POLYSILANE OLIGOMERS

[75] Inventors: Motoo Fukushima; Shigeru Mori, both of Kawasaki, Japan

[73] Assignee: Shin-Etsu Chemical Company, Limited, Tokyo, Japan

[21] Appl. No.: 32,109

[22] Filed: Mar. 17, 1993

[30] Foreign Application Priority Data

Mar. 17, 1992 [JP] Japan .................................. 4-091903

[51] Int. Cl.$^5$ .................................................. C07F 7/08
[52] U.S. Cl. .................................................. 556/430
[58] Field of Search .................................. 556/430

[56] References Cited

PUBLICATIONS

Chen and West, Organometallic Synthesis, 4, pp. 506-507 (1988).
Yamamoto et al, Journal of Organometallic Chemistry, vol. 23, pp. C7-C8 (1970).

*Primary Examiner*—Paul F. Shaver
*Attorney, Agent, or Firm*—Birch, Stewart, Kolasch & Birch

[57] ABSTRACT

There is disclosed a method for preparing a polysilane oligomer having a terminal SiH group represented by the structural formula (1):

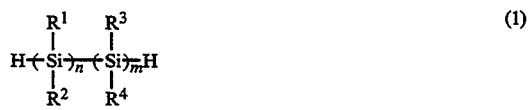

wherein $R^1$ to $R^4$ are monovalent hydrocarbon groups with proviso that at least one of $R^1$ to $R^4$ is an aryl group, n and m are integers of 1 or more, and n+m is equal to 3, 4, 5 or 6 comprising the step of reacting a disilane of the structural formula (2):

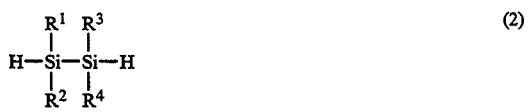

wherein $R^1$ to $R^4$ are as defined above in the presence of a Group VIII transition metal complex catalyst.

3 Claims, No Drawings

PREPARATION OF POLYSILANE OLIGOMERS

BACKGROUND OF THE INVENTION

1. Field of the Invention

This invention relates to a commercially advantageous method for preparing polysilane oligomers which are useful intermediates for the synthesis of conducive materials.

2. Prior Art

Oligosilanes having 3 to 5 silicon atoms were prepared in the prior art by reacting chlorosilanes in the presence of alkali metal catalysts in accordance with the following reaction scheme (R. West, Organometallic Synthesis, 1988, 4, pp. 506–507).

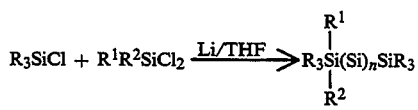

However, since the alkali metal must be used in an equimolar amount to the moles of chlorine in the starting reactant or chlorosilane, this method requires strict shielding of water and is thus undesirably cumbersome in operation. In particular, oligosilanes having a terminal SiH group can be synthesized only in low yields because the Si—H group of dimethylchlorosilane used as the starting reactant is susceptible to decomposition during the reaction.

Kumada et al reported disproportionation of pentamethyldisilane and sym-tetramethyl-disilane catalyzed by platinum complexes (J. Organometal. Chem., 23 (1970) C7–C8).

However, this method has an industrial problem since it employs a sever reaction condition such that pentamethyldisilane is heated in a sealed glass tube at 90° C. for 18 hours.

There is a need to have a commercially advantageous method for preparing polysilane oligomers.

SUMMARY OF THE INVENTION

Therefore, an object of the present invention is to provide a simple method capable of synthesizing polysilane oligomers in high yields.

The present invention is directed to a method for preparing a polysilane oligomer having a terminal SiH group represented by the structural formula (1):

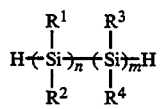

$R^1$ to $R^4$ are monovalent hydrocarbon groups with proviso that at least one of $R^1$ to $R^4$ is an aryl group, n and m are integers of 1 or more, and n +m is equal to 3, 4, 5 or 6. According to the present invention, a disilane of the structural formula (2):

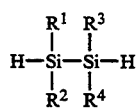

wherein $R^1$ to $R^4$ are as defined above is reacted in the presence of a Group VIII transition metal complex catalyst. Without resorting to the cumbersome operation of shielding against water, the inventive method is successful in preparing a polysilane oligomer having a terminal SiH group in high yields by carrying out reaction in a simple manner under moderate conditions.

DETAILED DESCRIPTION OF THE INVENTION

The polysilane oligomer preparing method according to the present invention starts with a disilane of the structural formula (2).

In the formula, $R^1$ to $R^4$ are monovalent hydrocarbon groups, preferably having 1 to 12 carbon atoms, for example, alkyl, cycloalkyl, aryl and aralkyl groups. Typical examples include methyl, ethyl, propyl, butyl, hexyl, cyclohexyl, phenyl, tolyl, xylyl, and naphthyl groups. At least one of $R^1$ to $R^4$ is an aryl group preferably having 6 to 12 carbon atoms such as phenyl, tolyl, xylyl and naphtyl group. Those disilanes of formula (2) are more advantageous because the end disilanes can be obtained in higher yields.

Preferably, the silane has the following structural formula (2a) in which $R^1=R^3$ and $R^2=R^4$.

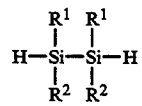

wherein $R^1$ and $R^2$ are monovalent hydrocarbon groups with proviso that at least one of $R^1$ and $R^2$ is an aryl group.

Illustrative examples of the disilane of formula (2) are 1,3-dimethyl-1,3-diphenyl-disilane, 1,3-diethyl-1,3-diphenyldisilane, and 1,1,3,3-tetraphenyldisilane.

The disilane can be synthesized, for example, by reacting a corresponding chlorosilane with an alkali metal such as sodium and lithium for desalting as shown by the following reaction scheme.

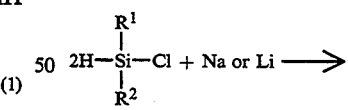

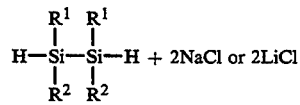

Suitable conditions may be selected for the reaction between chlorosilane and alkali metal. Often, the chlorosilane and alkali metal are used in a molar ratio of about 1:1.1. Reaction is effected in toluene solvent at 100° C. to 120° C. for ½ to 5 hours when the alkali metal is sodium. And, reaction is effected in polar solvents such as diethyl ether and tetrahydrofuran at −76° C. to 25° C. for ½ to 16 hours when the alkali metal is lithium.

According to the present invention, the disilane of formula (2) is reacted in the presence of a Group VIII transition metal complex catalyst which is a complex between a Group VIII transition metal such as nickel, palladium and platinum and ligands such as halogens, olefins, phosphines, amines and acetonitriles.

Preferred complexes are of the following formula (3):

$$MCl_2(R_3P)_2 \tag{3}$$

wherein M is nickel, palladium or platinum and R groups are identical or different monovalent hydrocarbon groups having 1 to 7 carbon atoms, such as methyl, ethyl, propyl, butyl, phenyl and tolyl groups. Examples of the complex of formula (3) include $PtCl_2[P(C_2H_5)_3]_2$, $NiCl_2[P(C_2H_5)_3]_2$, $PdCl_2[PPh_3]_2$, $NiCl_2[PPh_3]_2$, etc. wherein Ph is phenyl.

Preferably the complex is added in an amount of about 0.01 to 10 mol %, especially about 0.1 to 1 mol % of the disilane reactant. Less than 0.01 mol % of the complex would provide less reactivitity, requiring a long time until the reaction is complete. More than 10 mol % of the complex is not recommended from the economy because the complex is expensive.

Suitable conditions may be selected for the reaction between the disilane of formula (2) and the Group VIII transition metal complex catalyst. Typical reaction conditions include an inert gas atmosphere such as nitrogen gas and a temperature of 30° to 120° C. Especially for 1,3-dimethyl-1,3-diphenyldisilane, the typical procedure is heating and agitation at its reflux temperature for about ½ to 8 hours, preferably about ½ to 2 hours.

At the end of reaction, the by-products are removed from the reaction system and the reaction mixture is purified as by vacuum distillation. Then the end polysilane oligomer of formula (1) having a terminal SiH group is obtained.

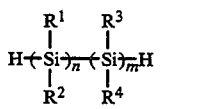
(1)

In the formula, letters n and m are integers of 0 or more, and n+m is 3, 4, 5 or 6, preferably 3, 4 or 5.

When the silane of formula (2a) is used as a starting material, the end polysilane oligomer of formula (1a) is obtained.

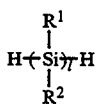
(1a)

wherein letter l is an integer of 3, 4, 5 or 6, preferably 3, 4 or 5.

Examples of the polysilane of formula (1) include triphenyltrimethyltrisilane, tetraphenyltetramethyltetrasilane, etc.

The polysilane oligomer produced by the method of the invention is a polymer of formula (1), that is, a trisilane, tetrasilane, pentasilane or heptasilane alone or a mixture of two or more of these polymers.

The polysilane oligomers of formula (1) having a terminal SiH group produced by the method of the invention can be converted, for example, into oligosilanes having a terminal chloro group by reacting them with chlorine or organic halides such as carbon tetrachloride, into which oligosilanes an organic group can be incorporated by reacting them with carbanions such as Grignard reagents and organic lithium compounds. It is also possible to react the polysilane oligomers of formula (1) with compounds having a vinyl or acetylenyl group for hydrosilylation, thereby forming a Si—C bond as shown by the reaction scheme below. By selectively reacting the oligomers with carbanions or acetylene compounds in this way, there can be synthesized polymers possessing alternately a C—C multiple bond and a Si—Si bond, which are currently regarded as promising conductive material. In this regard, the polysilane oligomers produced by the method of the invention are useful intermediates for the synthesis of conductive materials.

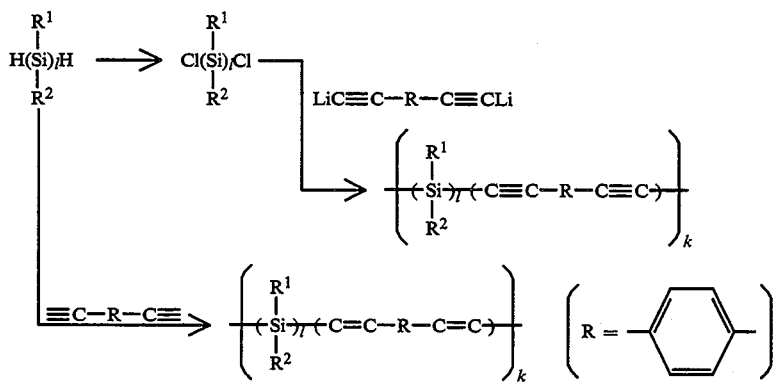

ADVANTAGES

The method of the present invention can synthesize polysilane oligomers of formula (1) having a terminal SiH group in high yields through simple operation and under moderate reaction conditions. The resultant polysilane oligomers are useful intermediates for the synthesis of promising conductive materials or polymers possessing alternately a C—C multiple bond and a Si—Si bond. Therefore, the method is of great commercial value.

EXAMPLES

Examples of the present invention are given below by way of illustration and not by way of limitation.

Example 1

To 2.32 grams (0.01 mol) of 1,3-dimethyl-1,3-diphenyldisilane was added 9.4 mg (0.019 mmol, 0.2 mol %) of $PtCl_2[P(C_2H_5)_3]_2$ in an argon atmosphere. In a nitrogen gas flow, the mixture was heated and agitated at 90° C. for one hour. After the methylphenylsilane by-product was removed from the system, the reaction mixture was worked up by vacuum distillation, obtaining a polysilane oligomer as a mixture of the following compounds.

|  | Amount | Yield |
| --- | --- | --- |
| Compound 1: triphenyltrimethyltrisilane | 0.40 g | 11% (1.1 mmol) |
| Compound 2: tetraphenyltetramethyltetrasilane | 0.62 g | 13% (1.3 mmol) |

Example 2

The procedure of Example 1 was repeated except that 5.5 mg (0.015 mmol, 0.15 mol %) of $NiCl_2[P(C_2H_5)_3]_2$ was used instead of $PtCl_2[P(C_2H_5)_3]_2$. There was obtained a mixture of 0.7 grams (yield 20%) of Compound 1 (triphenyltrimethyltrisilane) and 0.5 grams (yield 10%) of Compound 2 (tetraphenyltetramethyltetrasilane).

Comparative Example

The procedure of Example 1 was repeated except that 1.18 g (0.01 mol) of 1,1,3,3-tetramethyldisilane was used instead of 1,3-dimethyl-1,3-diphenyldisilane. There was obtained gaseous dimethylsilane as the main product. It seems that the reason why gaseous dimethylsilane was produced as the main product in this reaction is due to the reaction condition that the reaction was conducted in a nitrogen gas flow which is quite different from the reaction condition of Kumada et al that the reaction is conducted in a sealed glass tube.

After the completion of the reaction, the reaction mixture was distilled thereby obtaining only 0.3 (1.3 mmol, yield 13%) of the mixture of hexamethyltrisilane, octamethyltetrasilane and decamethylpentasilane.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for preparing a polysilane oligomer having a terminal SiH group represented by the structural formula (1):

wherein $R^1$ to $R^4$ are monovalent hydrocarbon groups with the proviso that at least one of $R^1$ to $R^4$ is an aryl group, n and m are integers of 1 or more, and n+m is equal to 3, 4, 5 or 6 comprising the step of reacting a disilane of the structural formula (2):

wherein $R^1$ to $R^4$ are as defined above, in the presence of a Group VIII transition metal complex catalyst of the formula:

$$MCl_2(R_3P)_2 \quad (3)$$

wherein M is nickel, palladium or platinum and R is a monovalent hydrocarbon group having 1 to 7 carbon atoms, in an inert gas flow atmosphere at a temperature of 30° to 120° C. for ½ to 8 hours.

2. The method of claim 1 wherein the complex is selected from the group consisting of $PtCl_2[P(C_2H_5)_3]_2$, $NiCl_2[P(C_2H_5)_3]_2$, $PdCl_2[PPh_3]_2$ and $NiCl_2[PPh_3]_2$ wherein Ph is phenyl.

3. The method of claim 1 wherein the complex is used in an amount of about 0.01 to 10 mol % based on the moles of the disilane.

* * * * *